(12) United States Patent
Hatano et al.

(10) Patent No.: US 12,303,100 B2
(45) Date of Patent: May 20, 2025

(54) ENDOSCOPE AND METHOD FOR CONFIRMING GROUNDING OF ENDOSCOPE

(71) Applicant: OLYMPUS CORPORATION, Hachioji (JP)

(72) Inventors: Keisuke Hatano, Fuchu (JP); Takuya Ariyoshi, Hino (JP); Hiroyuki Nagamizu, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 715 days.

(21) Appl. No.: 17/519,281

(22) Filed: Nov. 4, 2021

(65) Prior Publication Data

US 2022/0099758 A1 Mar. 31, 2022

Related U.S. Application Data (63) Continuation of application No. PCT/JP2019/018297, filed on May 7, 2019.

(51) Int. Cl.
*A61B 1/00* (2006.01)
*A61B 1/05* (2006.01)
*G01R 31/52* (2020.01)

(52) U.S. Cl.
CPC ...... *A61B 1/00057* (2013.01); *A61B 1/00114* (2013.01); *A61B 1/05* (2013.01); *G01R 31/52* (2020.01)

(58) Field of Classification Search
CPC ... A61B 1/00057; A61B 1/00114; A61B 1/05; A61B 1/0011; A61B 1/00112; G01R 31/50–52
See application file for complete search history.

(56) References Cited

U.S. PATENT DOCUMENTS

2013/0050457 A1\* 2/2013 Murayama ......... A61B 1/00124
348/75
2013/0150667 A1 6/2013 Mitamura et al.
(Continued)

FOREIGN PATENT DOCUMENTS

EP 2638841 A1 9/2013
EP 2674095 A1 12/2013
(Continued)

OTHER PUBLICATIONS

Jul. 9, 2019 International Search Report issued in International Patent Application No. PCT/JP2019/018297.
(Continued)

*Primary Examiner* — John P Leubecker
*Assistant Examiner* — Li-Ting Song
(74) *Attorney, Agent, or Firm* — Oliff PLC (57) ABSTRACT

An endoscope can include an internal member provided at a distal end of an insertion portion a conductive external member fitted over the internal member and electrically connected to a ground. The endoscope can also include an image pickup instrument fixed to the internal member, and the image pickup instrument can include a lens. The endoscope can include an electrical connection part having a first end portion connected to the conductive member and a second end portion connected to the external member, the electrical connection part being configured to electrically connect the conductive member and the external member, a conductor wire including a third end portion electrically connected to the first end portion, and a fourth end portion that passes through an opening formed in the external member.

19 Claims, 5 Drawing Sheets

(56) References Cited

U.S. PATENT DOCUMENTS

| | | | |
|---|---|---|---|
| 2013/0303853 A1 | 11/2013 | Takahashi et al. | |
| 2015/0230692 A1* | 8/2015 | Matsuda | A61B 1/00096 600/110 |
| 2017/0265715 A1 | 9/2017 | Nishina et al. | |
| 2020/0015664 A1* | 1/2020 | Hatase | A61B 1/07 |
| 2022/0409174 A1* | 12/2022 | Kinomoto | A61B 1/00096 |

FOREIGN PATENT DOCUMENTS

| | | |
|---|---|---|
| EP | 3213667 A1 | 9/2017 |
| JP | H06-034764 A | 2/1994 |
| JP | 2001-269309 A | 10/2001 |
| JP | 2013-198566 A | 10/2013 |
| JP | 2014-132923 A | 7/2014 |
| JP | 2015-016240 A | 1/2015 |
| JP | 2015-039410 A | 3/2015 |
| JP | 2017-200597 A | 11/2017 |
| JP | 2017-209278 A | 11/2017 |
| WO | 2012-124526 A1 | 9/2012 |
| WO | 2013-035379 A1 | 3/2013 |
| WO | 2013-084548 A1 | 6/2013 |
| WO | 2016-203830 A1 | 12/2016 |

OTHER PUBLICATIONS

Apr. 28, 2024 Office Action issued in Chinese Patent Application No. 201980095187.9.

* cited by examiner

ENDOSCOPE AND METHOD FOR CONFIRMING GROUNDING OF ENDOSCOPE

CROSS REFERENCE TO RELATED APPLICATION

This application is a continuation application of PCT/JP2019/018297 filed on May 7, 2019, the entire contents of which are incorporated herein by this reference.

BACKGROUND OF THE INVENTION

1. Field of the Invention

The present invention relates to an endoscope with an image pickup instrument mounted on a non-conductive frame component provided at a distal end portion of an insertion portion, and more specifically, to an endoscope configured to confirm electrical continuity of grounding of an image pickup instrument and a method for confirming grounding of an endoscope.

2. Description of the Related Art

As is well known, endoscopes are widely used for observation, treatment or the like of a living body (inside of a body cavity) or inspection, repair or the like of an inside of industrial plant equipment. Such endoscopes are provided with insertion portions for inserting into bent conduits.

As such an endoscope, a configuration with an image pickup instrument provided at a distal end portion of the insertion portion is known. In order to prevent static electricity, high frequency current or the like applied to the distal end portion from flowing to the image pickup instrument and causing a defect, the endoscope needs to allow the static electricity, high frequency current or the like to escape to the ground (GND) of the apparatus.

Leakage of static electricity or high frequency when a distal end rigid member is formed of an insulator is realized together with a diameter reduction of the distal end portion.

For example, International Publication No. 2012-124526 discloses an endoscope including a frame member of an observation optical system included in an insulating distal end rigid portion provided at an insertion portion and a connector member connected to a ground, in which a grounding metal member forming a structure of the insertion portion and a conductive connection part are connected in order from the connector member side.

As described in International Publication No. 2012-124526, when the distal end portion of the insertion portion is formed of an insulating member, as a method for grounding the image pickup instrument, it is necessary to electrically connect an exterior metal of the image pickup instrument and the ground (GND) of the endoscope via a conductor.

SUMMARY

An endoscope can include an internal member provided at a distal end of an insertion portion a conductive external member fitted over the internal member and electrically connected to a ground. The endoscope can also include an image pickup instrument fixed to the internal member, and the image pickup instrument can include a lens. The endoscope can include an electrical connection part having a first end portion connected to the conductive member and a second end portion connected to the external member, the electrical connection part being configured to electrically connect the conductive member and the external member, a conductor wire including a third end portion electrically connected to the first end portion, and a fourth end portion that passes through an opening formed in the external member.

An endoscope can also include an internal member provided at a distal end of an insertion portion, a conductive external member including an opening, fitted over the internal member and electrically connected to a ground that serves as an electrical reference, an image pickup instrument held to the internal member, a conductive member provided at the image pickup instrument, an electrical connection part configured to electrically connect the conductive member and the external member, and a conductor wire electrically connected to the conductive member, in which the opening is formed and a part of the conductor wire can pas through the opening.

A method for confirming grounding of an endoscope can employ an endoscope including an internal member provided at a distal end of an insertion portion, a conductive external member fitted over the internal member and electrically connected to a ground that serves as an electrical reference, an image pickup instrument fixed to the internal member, a conductive member provided at the image pickup instrument, an electrical connection part having a first end portion connected to the conductive member and a second end portion connected to the external member, the second end portion being on an opposite side of the first end portion, the electrical connection part being configured to electrically connect the conductive member and the external member, a conductor wire having one end electrically connected to the first end portion, and an opening formed in the external member with the internal member fitted in the external member and configured to lead in/out another end portion of the conductor wire. The method for confirming grounding of the endoscope can include sandwiching the second end portion of the electrical connection part between an outer surface of the internal member and an inner surface of the external member and fitting the internal member into the external member so that the other end of the conductor wire is led out from the opening, applying a tester to the other end of the conductor wire and the external member, and conducting a continuity test between the image pickup instrument and the external member with the electrical connection part and a step of accommodating the conductor wire through the opening in the external member after the continuity test.

DETAILED DESCRIPTION OF EXEMPLARY EMBODIMENTS

Note that in the following description, drawings based on each embodiment are schematic ones and a thickness-width relationship among components and thickness ratios among the components are different from the actual relationships and ratios, and there are cases where dimensional relationships and ratios differ among drawings.

The endoscope according to exemplary embodiments is an endoscope, an insertion portion of which has a small diameter, such as a bronchoscope or a uroscope. However, without being limited to this, the invention is also applicable to a so-called flexible scope, an insertion portion of which is flexible so as to be inserted into an upper or lower digestive organ or a so-called rigid endoscope, an insertion portion of which is rigid, so as to be used for surgery.

Hereinafter, an endoscope according to an aspect of the present invention will be described based on the accompanying drawings.

Figure 1:
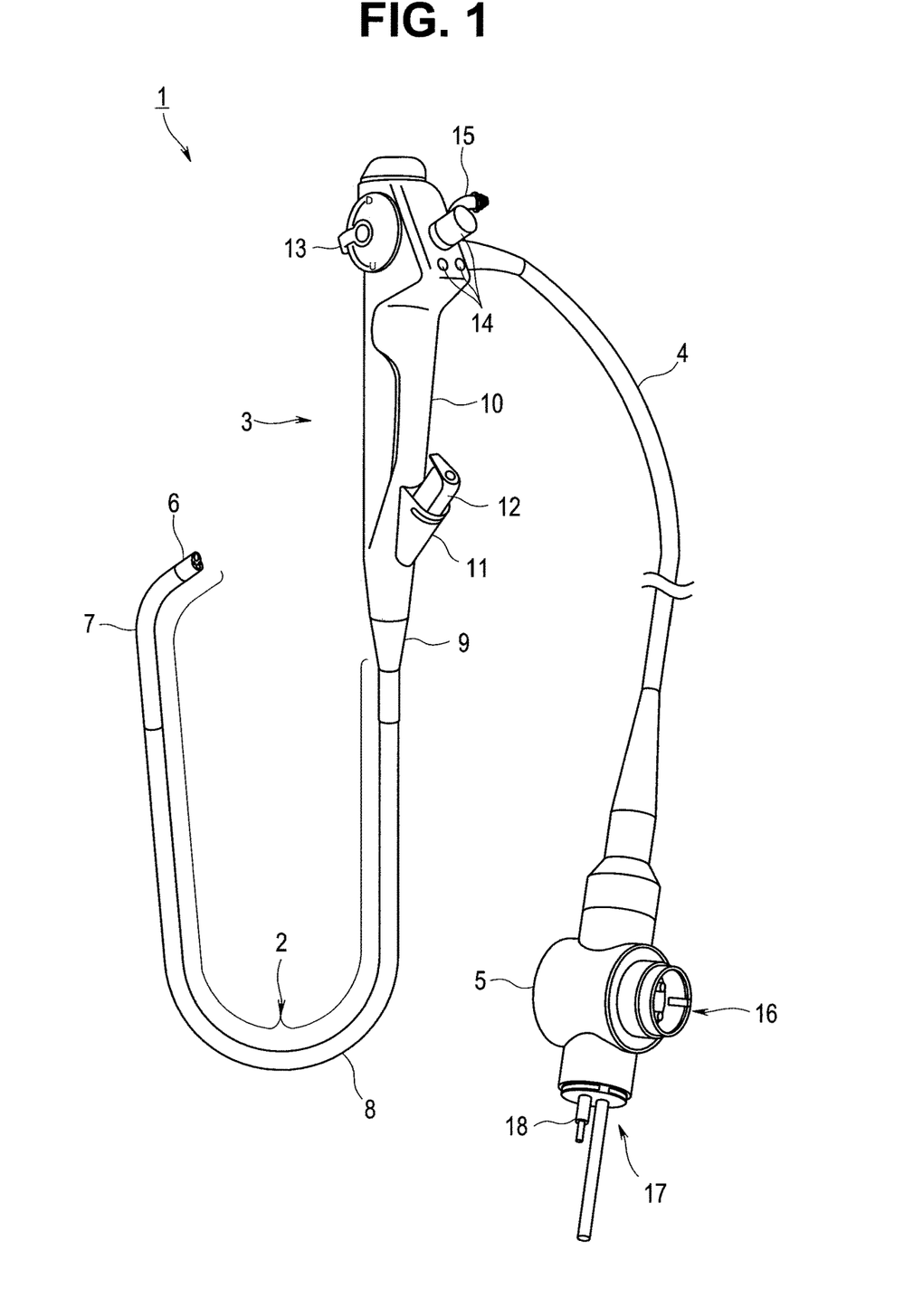
FIG. 1 is a diagram illustrating an appearance of an endoscope according to an exemplary embodiments.

As illustrated in FIG. 1, an endoscope 1, which is an electronic endoscope of the present embodiment, is mainly constructed of an insertion portion 2 formed in an elongated tubular shape, an operation portion 3 connected to a proximal end of the insertion portion 2, a universal cord 4, which is an endoscope cable that extends from the operation portion 3 and an endoscope connector 5 or the like disposed at a distal end of the universal cord 4.

The insertion portion 2 is a flexible tubular member formed by connecting a distal end portion 6, a bending portion 7 and a flexible tube portion 8 in order from a distal end side. Of the components, the distal end portion 6 accommodates and disposes an image pickup instrument, which is an image pickup apparatus incorporating image pickup means and which will be described later, and illumination means or the like.

The bending portion 7 is a mechanical part configured to allow the insertion portion 2 to be actively bent in two directions, up and down (UP-DOWN) by rotating operation of a bending lever 13 among operation members of the operation portion 3.

Note that the bending portion 7 is not limited to a type of bending portion that is actively bent in two directions, up and down, but may also be a type of bending portion that can be bent in four directions including left and right directions in addition to the up and down directions (in all directions around the axis, UP-DOWN/LEFT-RIGHT through up-down, left-right operations) or may be a type of bending portion that can be bent only in one (UP) direction or may be a type of bending portion that is simply passively bent without having any mechanism to actively bend the bending portion by the bending lever 13.

The flexible tube portion 8 is a tubular member formed with flexibility so as to be passively made flexible. In addition to a treatment instrument insertion channel, which will be described later, a signal cable bundle, which will be described later, and extends from the image pickup apparatus incorporated in the distal end portion 6 and further extends from the operation portion 3 to the inside of the universal cord 4, and a light guide bundle, which will be described later, and guides illumination light from a light source apparatus to be emitted from the distal end portion 6, and the like are inserted through the flexible tube portion 8 (none of the above-described components is shown here).

The operation portion 3 is constructed of a bend preventing portion 9 provided on a distal end side and connected to the flexible tube portion 8 by covering a proximal end of the flexible tube portion 8, a grasping portion 10 connected to the bend preventing portion 9 and grasped by the user's hand when using the endoscope 1, operation means for operating various endoscope functions provided on an outer surface of the grasping portion 10, a treatment instrument insertion portion 11 and a suction valve 15 and the like.

Examples of the operation means provided in the operation portion 3 include the bending lever 13 that performs bending operation of the bending portion 7 and a plurality of operation members 14 for performing operations corresponding to air/water feeding operation or suction operation, image pickup means, illumination means and the like.

The treatment instrument insertion portion 11 is a component provided with a treatment instrument insertion port through which various treatment instruments (not shown) are inserted and configured to communicate with the treatment instrument insertion channel (not shown) inside the operation portion 3 via a branching member.

The treatment instrument insertion portion 11 is provided with a forceps plug 12, which is a lid member to open/close the treatment instrument insertion port and configured to be attachable/detachable (replaceable) to/from the treatment instrument insertion portion 11. Note that the treatment instrument insertion channel is configured to also communicate with the suction valve 15 by the branching member inside the operation portion 3.

The universal cord 4 is a composite cable through which a signal cable bundle, a light guide bundle configured to transmit illumination light from a light source apparatus (not shown), and the like are inserted. The signal cable bundle, the light guide bundle, and the like are passed from the distal end portion 6 of the insertion portion 2 to the endoscope connector 5 via the operation portion 3 and the universal cord 4.

The endoscope connector 5 includes an electric connector portion 16 to which a signal cable for connection with a video processor (not shown) as an external device is connected on a side surface, a light source connector portion 17 to which a light guide bundle, which will be described later, for connection with the light source apparatus as an external device and an electric cable (not shown) are connected and an air/water feeding plug 18 to connect an air/water feeding tube (not shown) from an air/water feeding apparatus (not shown) as an external device or the like.

Here, a configuration of a distal end portion of the insertion portion 2 of the endoscope 1 of the present embodiment will be described based on FIG. 2 and FIG. 3. Note that description of a well-known configuration of the insertion portion 2 is omitted.

Figure 2:
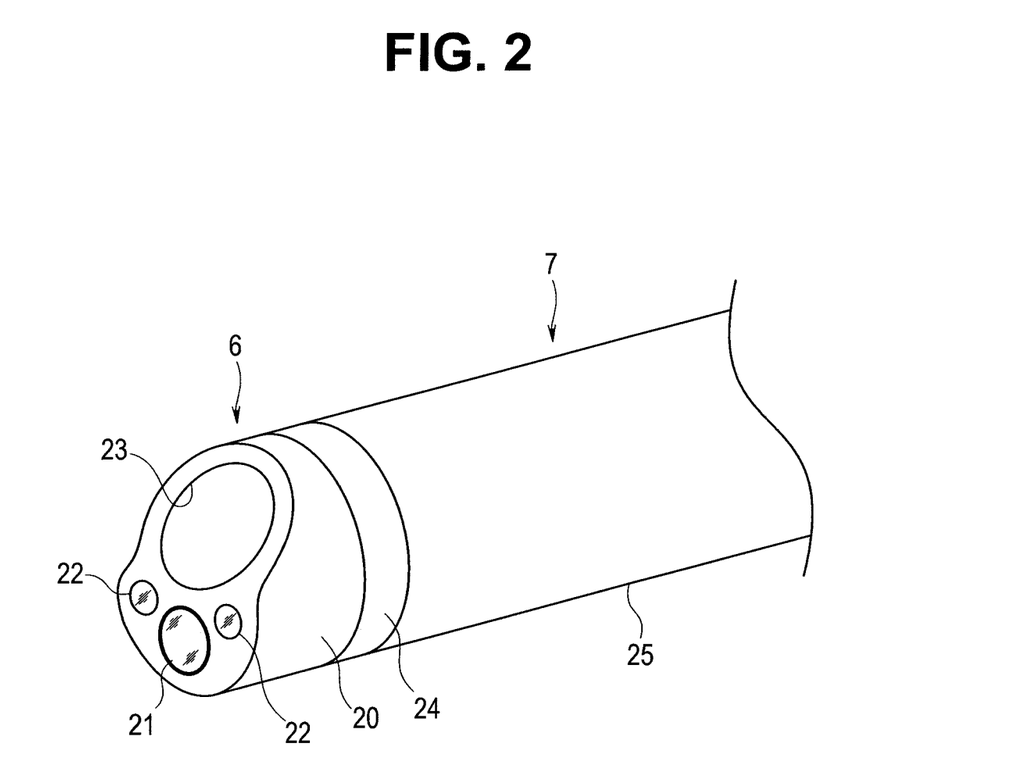
FIG. 2 is a perspective view illustrating a configuration of a distal end portion of an insertion portion of the endoscope according to the aspect of the present invention.

As illustrated in FIG. 2, the distal end portion 6 of the insertion portion 2 is provided with a distal end rigid portion 20 as an internal member, which is a frame component of an insulating non-conductive substantially columnar block body provided with an observation window 21, illumination windows 22 and a channel opening portion 23. The distal end rigid portion 20 is covered with curved rubber 25 from the middle to the proximal end side and the distal end of the curved rubber 25 is fixed by a thread winding adhesive part 24.

Figure 3:
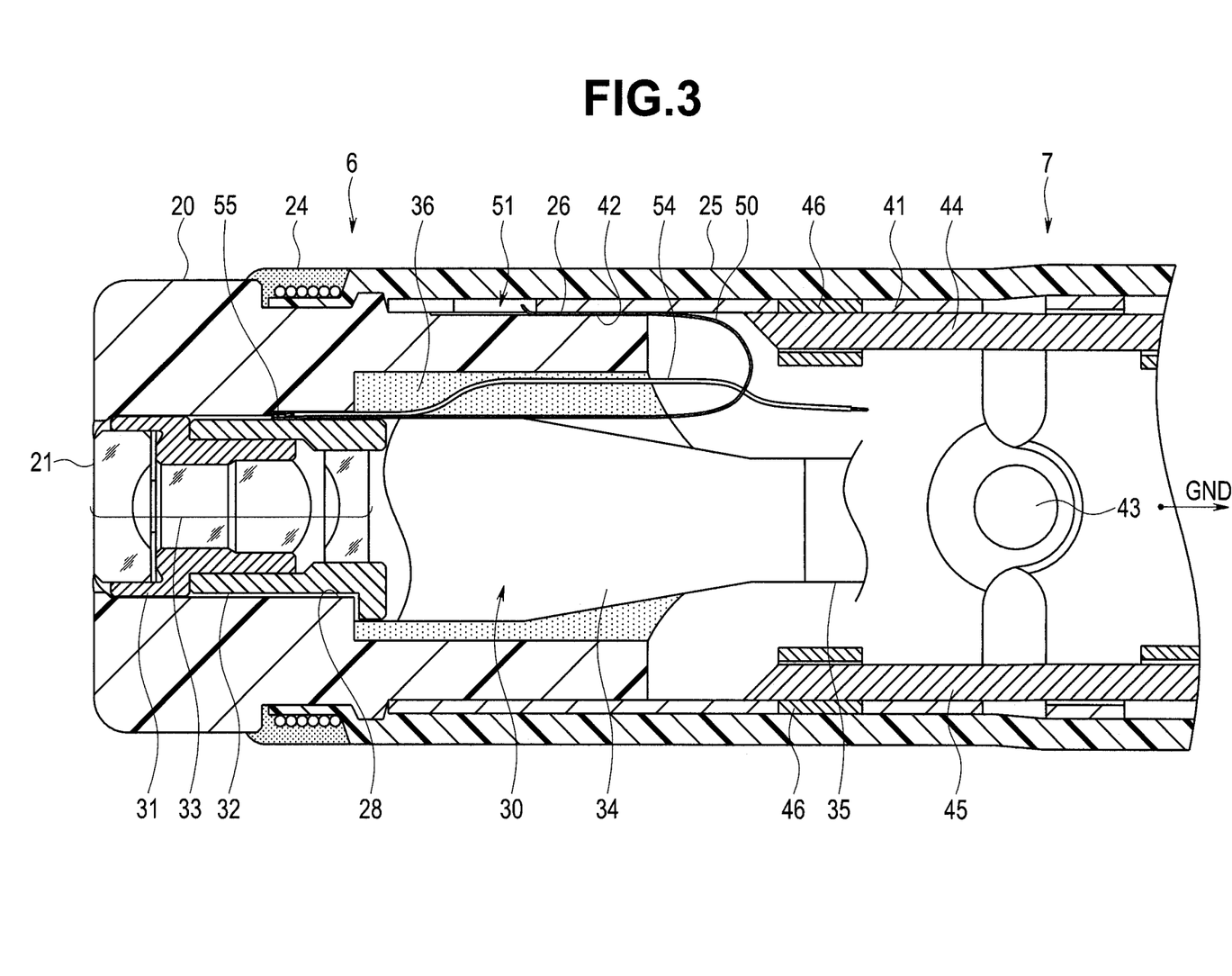
FIG. 3 is a cross-sectional view illustrating a configuration of the distal end portion of the insertion portion of the endoscope according to exemplary embodiments.

At the distal end portion 6, as illustrated in FIG. 3, an image pickup instrument 30 is fitted in a fitting hole 28 formed in the distal end rigid portion 20. The image pickup instrument 30 is fixed to the distal end rigid portion 20 with a filler 36 such as an adhesive.

The image pickup instrument 30 includes two lens frames 31 and 32, which are conductive parts made of conductive metals or the like configured to hold an objective lens group 33 including the observation window 21. The image pickup instrument 30 also includes a thermal contraction tube 34 configured to cover an element frame (not shown) provided with a solid image pickup device such as a CCD or CMOS and a drive circuit board together with a proximal end outer peripheral portion of the lens frame 32 on the proximal end side.

An image pickup cable 35 extends from the thermal contraction tube 34 on the proximal end side. Note that the inside of the thermal contraction tube 34 is filled with an adhesive or the like for watertightness.

A distal end of a jumper wire 50 as an electrical connection part and a core wire on a distal end side of an insulating cable 54 of a coated conductor wire with an insulating outer shell such as an enameled wire or vinyl-coated wire as a tester cable are electrically connected to the lens frames 31 and 32 of the image pickup instrument 30 by means of an electric connection part 55 such as solder.

The proximal end portion of the jumper wire 50 is electrically connected to a most distal end bending piece 41 as an external member, which is a conductive and annular exterior member, fitted over an outer peripheral portion 26 on the proximal end side of the distal end rigid portion 20.

Thus, a configuration of conduction is provided such that a current (charge) applied to the lens frames 31 and 32 flows to the jumper wire 50 and the bending piece 41.

The jumper wire 50 is held with the proximal end portion of the jumper wire 50 sandwiched between the outer peripheral portion 26, which is an outer surface of the distal end rigid portion 20, and an inner surface 42 of the most distal end bending piece 41. Thus, the jumper wire 50 is electrically conducted to the bending piece 41 and the lens frames 31 and 32 of the image pickup instrument 30 are electrically connected via the jumper wire 50.

Note that the proximal end of the insulating cable 54 is accommodated inside the insertion portion 2.

The bending piece 41 is made up of a plurality of pieces connected together and axially supported by a pivotally supporting part 43 so as to be rotatable with each other. Bending operations of the plurality of bending pieces 41 are performed by pulling/relaxing the bending operation wires 44 and 45 through operation of the bending lever 13.

Thus, the plurality of bending pieces 41 are caused to rotate around the pivotally supporting part 43, and the bending portion 7 is thereby bent. Note that the bending operation wires 44 and 45 are fixed to or inserted into or held to wire guides 46 provided on the inner surface side of the plurality of bending pieces 41.

The plurality of bending pieces 41 are electrically conducted to each other and connected so that the most proximal end bending piece 41 is electrically conducted to a metal braid (not shown) of the flexible tube portion 8. Note that the metal braid of the flexible tube portion 8 is also electrically conducted to the endoscope connector 5 via a metallic frame of the operation portion 3 and the universal cord 4.

The endoscope connector 5 is connected to an external device, and a patient ground (GND), which is used as an electrical reference for the endoscope, is electrically conducted to the image pickup instrument 30.

In other words, the endoscope 1 is configured such that an electrically conductive path of a ground (GND) is formed from the bending pieces 41 through the metal braid of the flexible tube portion 8, the frame of the operation portion 3, the universal cord 4 to the endoscope connector 5, and the endoscope connector 5 is connected to the external device and grounded.

Thus, the image pickup instrument 30 fitted in the non-conductive distal end rigid portion 20 is also inserted via the jumper wire 50 electrically connected to the most distal end bending piece 41, thus providing a configuration in which the endoscope connector 5 is connected to the external device and grounded.

Figure 4:
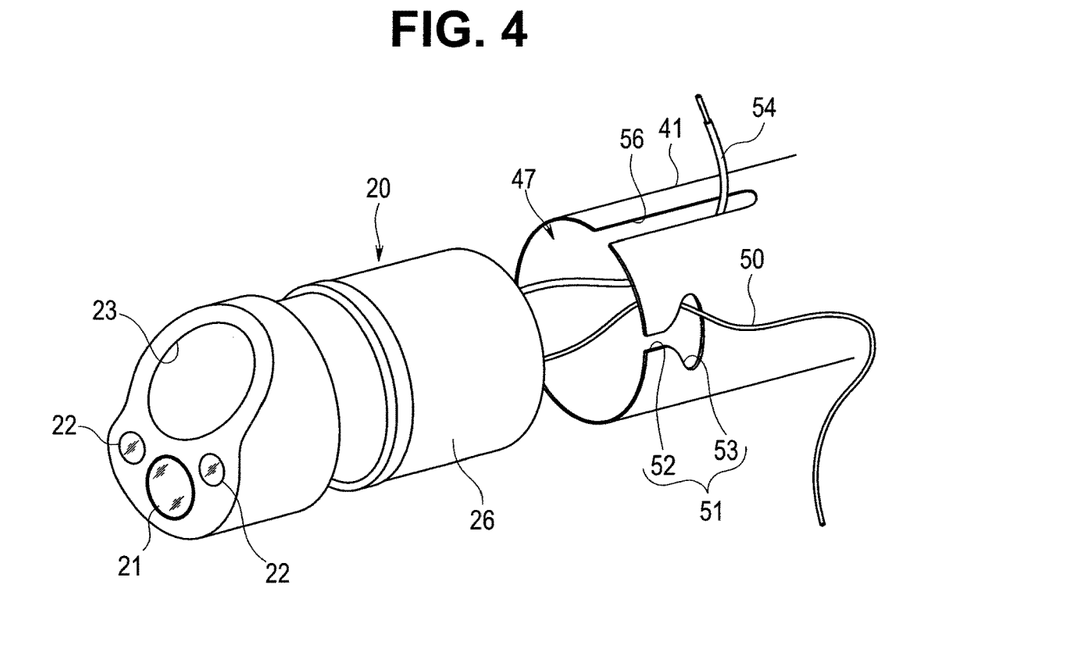
FIG. 4 is an exploded perspective view illustrating a distal end rigid portion fitted in a most distal end bending piece of the endoscope according to exemplary embodiments.
Figure 5:
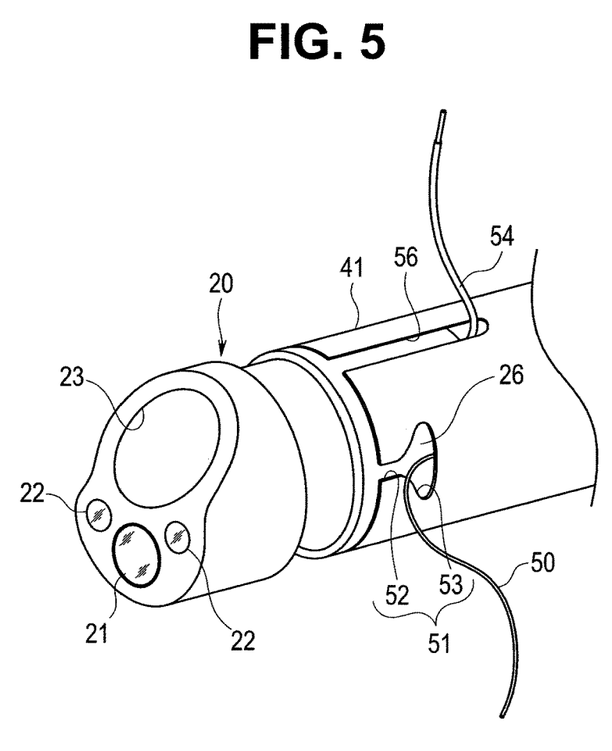
FIG. 5 is a perspective view illustrating the distal end rigid portion fitted in the most distal end bending piece of the endoscope according exemplary embodiments.

Note that an opening 51, which is an electrical connection part cut hole partially cut out from an end portion on the distal end side on which the distal end opening 47 (see FIG. 4) is provided toward a proximal end is formed in the most distal end bending piece 41 in which the distal end rigid portion 20 is fitted as illustrated in FIG. 4 and FIG. 5. The opening 51 exposes part of an outer circumferential surface of the distal end rigid portion 20.

As illustrated in FIG. 5, the opening 51 includes a linear groove portion 52 cut out from the distal end opening 47 at an end portion of the bending piece 41 toward the proximal end and a triangular electrical connection part cut portion 53 that communicates with the groove portion 52.

Furthermore, a notch 56 having a predetermined length cut out from the distal end opening 47 toward the proximal end is formed in the most distal end bending piece 41 in which the distal end rigid portion 20 is fitted. The notch 56 is intended to lead out the insulating cable 54 from the most distal end bending piece 41.

While the distal end rigid portion 20 is fitted in the most distal end bending piece 41, the notch 56 is set to a predetermined length larger than the length of the proximal end of the distal end rigid portion 20.

In other words, the notch 56 is set to the predetermined length, which is longer than the length of the part of the distal end rigid portion 20 fitted in the most distal end bending piece 41 so that a cable outlet of an opening from which the insulating cable 54 is led out is formed.

Note that the configuration in which the insulating cable 54 is led out need not necessarily be cut out from the distal end opening 47 of the most distal end bending piece 41, but a cable outlet having a hole shape to lead out the insulating cable 54 may be formed in the outer peripheral portion of the most distal end bending piece 41 that does not overlap the fitting part of the distal end rigid portion 20.

Here, as illustrated in FIG. 4 and FIG. 5, a configuration in which the distal end rigid portion 20 is fitted in the most distal end bending piece 41 and the jumper wire 50 that extends out of the opening 51 is cut will be described.

When the distal end rigid portion 20 is fitted into the most distal end bending piece 41, as illustrated in FIG. 4, the jumper wire 50 is passed from the groove portion 52 of the opening 51 of the bending piece 41 into the electrical connection part cut portion 53.

Note that since the jumper wire 50 can be passed into the electrical connection part cut portion 53 of the opening 51 of the bending piece 41, there may be no necessity for the groove portion 52 that communicates between the distal end opening 47 of the bending piece 41 and the opening 51.

As illustrated in FIG. 5, the distal end rigid portion 20 is fitted into the most distal end bending piece 41. At this time, the jumper wire 50 is sandwiched and fixed between the outer peripheral portion 26, which is the outer surface of the distal end rigid portion 20 and the inner surface 42 of the most distal end bending piece 41, and led out from the electrical connection part cut portion 53 of the opening 51.

Figure 6:
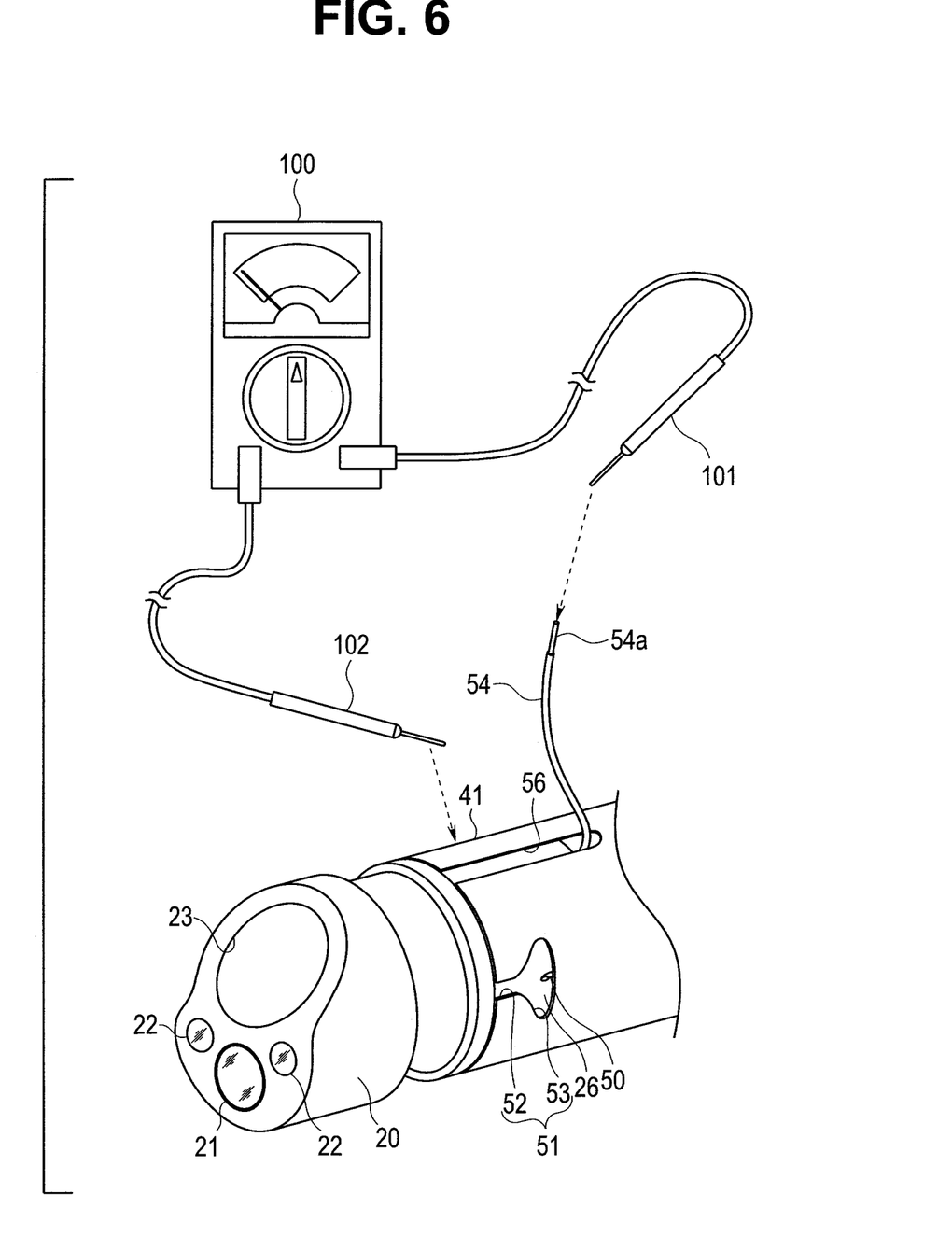
FIG. 6 is a diagram illustrating the distal end rigid portion fitted in the most distal end bending piece, continuity of which is tested using a tester, of the endoscope according to exemplary embodiments.

An extra portion of the jumper wire 50 that extends out of the electrical connection part cut portion 53 is cut using a cutting tool (not shown) such as a design knife so that the jumper wire 50 fits in the electrical connection part cut portion 53 as illustrated in FIG. 6.

In other words, when the distal end rigid portion 20 is fitted into the most distal end bending piece 41, the jumper wire 50 connected to the lens frames 31 and 32, which are conductive portions of the image pickup instrument 30, is configured to be sandwiched between the distal end rigid portion 20 and the bending piece 41 so that the jumper wire 50 can be electrically connected to the conductive bending piece 41 easily and reliably.

Thus, in the endoscope 1, even when static electricity, a high frequency current or the like generated from a treatment instrument or the like is applied to the distal end portion 6 of the insertion portion 2 where the non-conductive distal end rigid portion 20 is provided and flows to the lens frames 31 and 32 of the image pickup instrument 30, the high frequency current or the like is dropped from the jumper wire 50 to the ground (GND) via the bending piece 41.

In other words, a charge generated in the distal end portion 6 flows to the lens frames 31 and 32, and is leaked from the jumper wire 50 to the ground (GND) via the bending piece 41. Therefore, the image pickup instrument 30 of the endoscope 1 can prevent defects caused by static electricity, high frequency current or the like.

Therefore, the endoscope 1 is configured to have a simple structure in which in order to ground the image pickup instrument 30, a neighboring portion at one end of the jumper wire 50, which is a conductive wire, is sandwiched between the distal end rigid portion 20, which is a distal end frame component that insulates the image pickup instrument 30 from outside, and the bending piece 41, which is an exterior member connected to the ground (GND).

Note that the distal end rigid portion 20 is preferably non-conductive, but without being limited to this, the distal end rigid portion 20 may be conductive as well.

The distal end rigid portion 20 is fitted into the most distal end bending piece 41, and one tester rod 101 of a tester 100 is applied to a conductor wire 54a such as a copper wire stripped of coating such as enamel, sheath from the lead out end portion of the insulating cable 54 led out of the notch 56 formed in the most distal end bending piece 41. On the other hand, another tester rod 102 of the tester 100 is applied to the outer peripheral portion of the most distal end bending piece 41, and a continuity test between the image pickup instrument 30 and the most distal end bending piece 41 is conducted.

In other words, the image pickup instrument 30 is electrically connected to the most distal end bending piece 41 via the jumper wire 50, and one ends of the jumper wire 50 and the insulating cable 54 are connected to the lens frames 31 and 32 via the electric connection part 55.

Thus, by applying the tester rods 101 and 102 of the tester 100 to the conductor wire 54a of the insulating cable 54 and the most distal end bending piece 41, it is possible to conduct a continuity test of the jumper wire 50 that electrically connects the lens frames 31 and 32 of the image pickup instrument 30 and the most distal end bending piece 41 to ensure that there is an electrical connection between the lens frames 31 and 32 and the distal end bending piece 41 and inspect for a defect such as a wire breakage in the jumper wire 50.

Note that after the continuity test using the tester 100, the insulating cable 54 is accommodated from the cable outlet formed of the notch 56 in the most distal end bending piece 41. At this time, an uncoated conductor wire 54a of the insulating cable 54 may be cut off or an insulating sleeve may be provided at the end portion of the insulating cable 54.

Even after fitting the distal end rigid portion 20 into the most distal end bending piece 41, the endoscope 1 configured as described above can easily conduct a continuity test between the image pickup instrument 30 and the bending piece 41 conducted to the ground (GND), and confirm grounding of the image pickup instrument 30.

Therefore, the endoscope 1 can easily and reliably electrically connect the image pickup instrument 30 incorporated in the distal end portion 6 of the insertion portion 2 to the bending piece 41, which is the conductive portion conducted to the ground (GND) by the jumper wire 50 and can be configured to easily confirm grounding of the image pickup instrument 30 by conducting a continuity test with the tester 100 applied to the bending piece 41 and the insulating cable 54.

The invention described in the above embodiment is not limited to the above embodiment, but various modifications can be implemented without departing from the gist of the invention in the implementation phase. Furthermore, the above embodiment includes inventions in various phases and various inventions can be extracted according to appropriate combinations in a plurality of disclosed configuration requirements.

For instance, even when some configuration requirements are deleted from all the configuration requirements illustrated in the embodiments and modifications, configurations from which the configuration requirements are deleted can be extracted as inventions as long as the described problems can be solved and the described effects can be achieved.

What is claimed is:

1. An endoscope comprising:
    an internal member provided at a distal end of an insertion portion;
    a conductive external member fitted over an outer surface of the internal member and electrically connected to a ground that serves as an electrical reference;
    an image pickup instrument fixed to the internal member;
    a conductive member provided on the image pickup instrument;
    an electrical connection wire including a first portion connected to the conductive member and a second end portion connected to the external member, the second end portion located proximally relative to the first portion, the electrical connection wire being configured to electrically connect the conductive member to the external member;
    a conductor wire comprising a third portion and a fourth end portion, the third portion being electrically connected to the first portion of the electrical connection wire; and
    an opening formed in the external member with the internal member fitted in the external member, the fourth end portion of the conductor wire configured to pass through the opening.

2. The endoscope according to claim 1, wherein the internal member is non-conductive.

3. The endoscope according to claim 1, wherein the conductor wire is a coated conductor wire coated with an insulator.

4. The endoscope according to claim 1, wherein the image pickup instrument includes an image sensor.

5. A method for confirming grounding of an endoscope, the endoscope comprising:
an internal member provided at a distal end of an insertion portion;
a conductive external member fitted over an outer surface of the internal member and electrically connected to a ground that serves as an electrical reference;
an image pickup unit fixed to the internal member;
a conductive member provided at the image pickup instrument;
an electrical connection wire including a first portion connected to the conductive member and a second end portion connected to the external member, the second end portion located proximally relative to the first portion, the electrical connection wire being configured to electrically connect the conductive member to the external member;
a conductor wire having a third portion electrically connected to the first portion; and
an opening formed in the external member with the internal member fitted in the external member, the conductor wire including a fourth end portion configured to pass through the opening, the method comprising:
sandwiching the second end portion of the electrical connection wire between an outer surface of the internal member and an inner surface of the external member;
fitting the internal member into the external member so that the fourth end portion of the conductor wire passes through the opening;
applying a tester to the fourth end portion of the conductor wire and the external member; and
conducting a continuity test between the image pickup instrument and the external member with the electrical connection wire to ensure an electrical connection is not damaged.

6. The method for confirming grounding of an endoscope according to claim 5, wherein the conductor wire passes through the opening in the external member after the continuity test.

7. An endoscope comprising:
a lens;
a frame holding the lens;
an internal member holding the frame;
an external member fitted over an outer surface of the internal member; and
a first part of a first wire and a first part of a second wire located between the frame and the internal member, wherein a second part of the first wire is located between the internal member and the external member.

8. The endoscope according to claim 7, wherein when a charge is applied between the second wire and the external member, the charge flows from the second wire to the frame, and then to the first wire, and then to the external member.

9. The endoscope according to claim 7, wherein the external member includes a first opening.

10. The endoscope according to claim 9, the first opening is configured to receive a second part of the second wire.

11. The endoscope according to claim 9, wherein the external member includes a second opening, a second part of the first wire is exposed from the second opening.

12. The endoscope according to claim 11, wherein the second part of the first wire is located between the internal member and the external member.

13. The endoscope according to claim 7, wherein the frame is electrically connected to the external member via the first wire.

14. The endoscope according to claim 7, wherein a part of the second wire is covered by an insulator.

15. The endoscope according to claim 7, wherein the second wire is electrically connected to the first wire.

16. The endoscope according to claim 7, wherein the external member includes a second opening that exposes an outer circumferential surface of the internal member, and the second opening includes a linear groove portion and a triangular cut portion.

17. The endoscope according to claim 7, wherein the external member includes a plurality of pieces connected together and axially supported by a pivotally supporting part such that the plurality of pieces are configured to rotate relative to the pivotally supporting part.

18. The endoscope according to claim 7, wherein at least two sections of the first wire contact the internal member.

19. The endoscope according to claim 7, wherein the external member is connected to a ground that serves as an electrical reference.

* * * * *